United States Patent [19]

Chakrabarti et al.

[11] 4,283,321
[45] Aug. 11, 1981

[54] ALKYL ARYL ETHYLENEOXY SULFONATE SURFACTANTS FOR VINYL ACETATE POLYMERIZATION

[75] Inventors: Paritosh M. Chakrabarti, Wayne; Darrell G. Kirchner, Fairlawn, both of N.J.

[73] Assignee: GAF Corporation, New York, N.Y.

[21] Appl. No.: 81,367

[22] Filed: Oct. 3, 1979

[51] Int. Cl.$^3$ .............................................. C08L 31/04
[52] U.S. Cl. ..................... 260/29.6 MQ; 260/29.6 R; 260/505 R; 526/209; 526/222
[58] Field of Search .................. 260/29.6 MQ, 29.6 R

[56] References Cited

U.S. PATENT DOCUMENTS

| | | | |
|---|---|---|---|
| 2,115,192 | 4/1938 | Bruson | 260/512 R |
| 3,637,563 | 1/1972 | Christena | 260/29.6 R |
| 4,091,014 | 5/1978 | Johnson et al. | 260/512 R |

*Primary Examiner*—Harold D. Anderson
*Attorney, Agent, or Firm*—James Magee, Jr.; Sheldon Parker

[57] ABSTRACT

Improved surfactants can be produced from alkyl aryl poly(ethyleneoxy) sulfonates, represented by the formula:

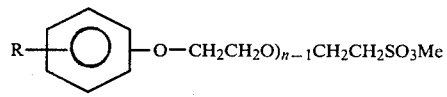

wherein:
R is an alkyl or dialkyl group having at least 6 carbon atoms; and
n is greater than 9; and
Me is a monovalent cation, preferably Na, NH$_4$, K or Li.

High solids content aqueous vinyl acetate emulsions having long term stability are provided by polymerizing vinyl acetate in the presence of the surfactant and water. The quantity of water is predetermined so as to produce a latex having at least 40% solids.

8 Claims, No Drawings

ALKYL ARYL ETHYLENEOXY SULFONATE SURFACTANTS FOR VINYL ACETATE POLYMERIZATION

CROSS REFERENCE TO RELATED APPLICATION

U.S. patent application, Ser. No. 081,322 filed concurrently with this application, disclosing and claiming different but related subject matter.

BACKGROUND OF THE INVENTION

1. Field of the Invention

The present invention relates to novel salts of alkyl aryl polyethyleneoxy sulfonates, their method of manufacture and their use as surfactants in poly vinyl acetate emulsions.

2. Description of the Prior Art

Surfactant sold under the trademark Triton by Rohm & Haas Co. and Alipal SE-463 by GAF Corp. are alkyl aryl polyether sulfonate, sodium salts. These sulfonates offer many diversified surfactant properties not commonly encountered in a single compound. They out perform comparable sulfates in offering resistance to decomposition under both highly acidic and basic conditions, thus being suitable in metal cleaning applications for either acid pickling baths or alkaline cleaning formulations. Their excellent compatibility with alkaline detergent builders and their excellent emulsifying character with fats, greases, oils and gelatins afford many applications possibilities in lime soap formulation, the film coating industry, as dye leveling agents, post-latex stabilizers and in emulsion polymerization. A major application for this type of surfactant is a shampoo base for the cosmetics industry where it finds wide applicability because of its detergent, lathering and solubilizing properties.

However, it has now been found that in certain applications, as for example the production of high solids content, poly vinyl acetate emulsions, coagulation occurs when attempting to produce emulsions having less than 40% water.

The production of high solids content latexes has long been considered to be desirable, the advantage being the maximizing use of production equipment and the minimization of the quantity of water which must be shipped in a latex. High solids content emulsions tend to coagulate immediate or become unstable after relatively short periods of storage. For example, in the production of vinyl acetate, the preparation of high solids content emulsions has necessitated the use of phosphate type surfactants, protective colloids and/or special processing, as disclosed for example in U.S. Pat. No. 3,637,563. The heretofore employed procedures and formulations have proven to be inadequate because of unfavorable economic factors and/or environmental considerations. Although it would be highly desirable to eliminate the use of a protective colloid thereby providing a cost reduction in the system, repeated attempts to produce such systems have proven unsuccessful. U.S. Pat. No. 3,637,563 which is directed to the production of high solid aqueous polymer emulsions suggests the use of surfactants such as, alkylphenoxy poly(ethyleneoxy) ethanols, as well as the use of higher molecular weight sulfates and sulfonates. Among the materials specifically referred to in the aforenoted patent are alkylphenoxy poly(ethyleneoxy) ethanols which contain from about 30 to about 100 ethyleneoxy units, and typical anionic surfactants, e.g., an ethoxylated higher fatty acid which has also been sulfonated. In order to produce a stable emulsion employing the disclosure of U.S. Pat. No. 3,637,563, it is necessary to employ one or more protective colloids, particularly when a reflux type polymerization is carried out using vinyl acetate, or the like, as part of the monomer charge. Included among such materials are either linkage containing protective colloids, such as hydroxy methyl cellulose, hydroxy ethyl cellulose, ethyl hydroxy ethyl cellulose, carboxy methyl cellulose, ethoxylated starch derivatives, and the like. Other protective colloid forming substances, i.e., those containing no ether linkages, are also disclosed as being usable, either alone or together with the aforementioned ether linkage-containing materials.

SUMMARY OF THE INVENTION

It has now been found that improved surfactants can be produced from alkyl aryl poly(ethyleneoxy) sulfonates, represented by the formula:

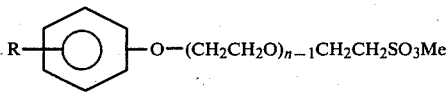

an alkyl or a dialkyl group having at least 6 carbon atoms; and n is greater than 9

Me is a monovalent cation, preferably Na, NH$_4$, K or Li

High solids content vinyl acetate latexes having high shelf-lives can be produced without the need to resort to special processing or protective colloids by employing the aforenoted sulfonates.

In accordance with the present invention, an improved high solids content aqueous vinyl acetate emulsion is provided by polymerizing vinyl acetate in the presence of the surfactant and water. The quantity of water is predetermined so as to produce a latex having at least 40% solids.

DESCRIPTION OF THE PREFERRED EMBODIMENTS

In order that those skilled in the art can more fully understand the present invention, the following detailed description and examples are provided. These examples are intended solely for the purpose of illustrating the invention, and are not to be construed as expressing limitations unless so set forth in the appended claims. All parts and percentages are by weight, unless otherwise stated.

Salts of non-ionic surfactants of the type sold under the trademark ALIPAL, by GAF Corporation, are generally recognized as having utility in emulsion polymerization. These surfactants are represented by the formula:

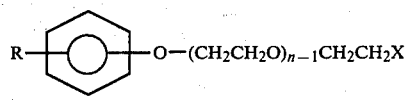

Commercial surfactants include ALIPAL SE-463, wherein R is $C_8H_{17}$, X is $SO_3Na_3$ and n is 3. It is seen in Table I, that the value of n is critical and that the use of an n value greater than 9, yields improved properties or otherwise unattainable properties.

The surfactants of Table I can all be represented by the formula:

$$R_2\text{-}(CH_2CH_2O)_{n-1}CH_2CH_2NaSO_3$$

In Alfol 1012, $R_2$ is a straight chain alcohol having an average of between 10 and 12 carbons and n is 3.

In Alfol 12, $R_2$ is a straight chain alcohol having 12 carbons and n is 4.

In Alfol 1214, $R_2$ is a straight chain alcohol having an average of 12 to 14 carbons and n is 6.

In oxotridecyl, $R_2$ is an oxotridecyl group and n averages about 4.2.

In Emulphogene BC-720, $R_2$ is oxotridecyl; and n is greater than 9.

In Igepal CO-630, R is nonyl phenoxy and n is 9.
In Igepal CO-850, R is nonyl phenoxy and n is 20.
In Igepal CO-890, R is nonyl phenoxy and n is 40.

The Emulphogene and Igepal are registered trademarks of GAF Corporation and Alfol is a trademark of Continental Oil Company.

Table I compares the use of various surfactants in the emulsion polymerization of vinyl acetate, surfactants having 9 or less repeating ethyleneoxy groups were found to be unable to give the results attainable with longer polymer chains. In one isolated, non-representative run, the Igepal 850 sulfonate failed to give the desired result.

Basically, the technology involves initially transforming the terminal alcohol functionality of a nonionic surfactant to a terminal chloride using thionyl chloride or other chlorinating agents, as follows:

$$RO(CH_2CH_2O)_nCH_2CH_2OH \xrightarrow{SOCl_2} RO(CH_2CH_2O)_nCH_2CH_2Cl \quad (1)$$

The chloride terminated material is then converted to the sodium sulfonate, using sodium sulfate, as follows:

$$RO(CH_2CH_2O)_nCH_2CH_2Cl \xrightarrow{Na_2SO_3} RO(CH_2CH_2O)_nCH_2CH_2SO_3Na \quad (2)$$

The sulfonate functionality has much less tendency to hydrolize in solutions of low pH than does an analagous surfactant with a sulfate functionality.

$$RCH_2SO_3Na \xrightarrow{H^+} \text{Stable (sulfonate)} \quad (3)$$

$$RCH_2OSO_3Na \xrightarrow{H^+} RCH_2OH \text{ (Sulfate decomposition)} \quad (4)$$

The ether sulfonates are noted to contain both an ethoxylated nonionic portion and a sulfonic acid anionic portion.

In the systems of Table I, the alkyl aryl poly ethoxy sulfonates were employed for producing poly vinyl acetate latexes, without the incorporation of a protective colloid. In each case, the alkyl sulfonates failed to produce a stable vinyl acetate latex in the absence of a protective colloid.

The criticality of the length of the poly ethoxy group is evident from the failure of the Igepal 630 sulfonate to produce a stable latex. By way of contrast, the sulfonate of Igepal CO-850 formed very stable vinyl acetate emulsions at 55 and 62% solids. The latexes exhibited good mechanical stability, no coagulum, low viscosity and excellent shelf life. The latex produced from the sulfonate of Igepal CO-890 coagulated after 24 hours storage, the probable contributing factor being the low conversion to the sulfonate form.

Looking now in greater detail to the chemistry of the production of the surfactants of the present invention it is noted that the synthetic approach to the production of poly ether sulfonate type surfactants involves the reaction of chlorine capped nonionics with sodium sulfite, as disclosed in U.S. Pat. No. 2,115,192.

$$R(OC_2H_4)_nCl + Na_2SO_3 \xrightarrow{OH^-}{H_2O} R(OC_2H_4)_nSO_3^-Na^+ + NaCl$$

The reaction requires high temperature—155°–170° C. being the most desirable range—and pressures of 70–115 psig. To attain over 90% conversion of the chlorine capped nonionics, reaction times of above about 10 hours are typical. The rate of sulfonation appears to be 100 to 500 times the rate of competive hydrolysis under proper reaction conditions such that good conversions can be expected with most under the reaction conditions to be defined in this report. The competing hydrolysis reaction results in a portion of OH terminated nonionics being present in the reaction product as depicted below.

$$R(OC_2H_4)_nCl \xrightarrow[\Delta]{OH^-/H_2O} R(OC_2H_4)_nOH \text{ (Hydrolysis)}$$

The sulfonate method of preparation is well-known to those skilled in the art as represented by patents such as U.S. Pat. Nos. 4,091,014; 2,209,911 and 2,148,432.

U.S. Pat. No. 4,091,014 is noted to disclose the manufacture of ether sulfonates, by sulfonating alcohols such as:

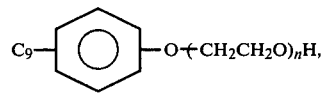

where n is an integer such as 3, 4 and 5. U.S. Pat. No. 2,209,911 discloses the production of alkylated phenoxy ether halides, while U.S. Pat. No. 2,148,432 discloses the method of producing alkyl phenoxy polyethylene oxide sulfonates from the corresponding alkyl phenoxy poly ethoxy halide. It should thus be evident that the sodium salts of polyether sulfonates of the present invention can be made in accordance with the teachings of the aforenoted patents.

Whereas the prior art typically is primarily concerned with an sulfonates having 2, 3 or 4 ethylene oxide unit, the instant invention is directed to higher values of "n". It appears that the ethylene oxide chain length has an effect on the rate of the sulfonation reaction, based on the unreacted sulfite present in a series of identical runs after a 10 hour reaction period at elevated temperature. It is believed that the steric hinderance of the polyethoxy group is a limiting factor in the sulfonate conversion and precludes adequate conversion of n=40 polyethyleneoxys to useful sulfonates.

The upper limit for the length of the ethylene oxide claim is not as critical as the lower limit. An upper limit for n, of about 30 is preferred, however, to the extent such a material could be made and isolated, an n value in excess of 40 could be used. It is preferable to balance the properties of the alkyl group and the polyethoxy group. Therefore, the alkyl group should have between 6 and 18 carbons and preferably no more than 12 carbons. While dialkyl groups can be employed, the number of carbons in each alkyl group should not be greater than 12. The conversions are listed below.

Igepal CO Series Conversions at 160° C.

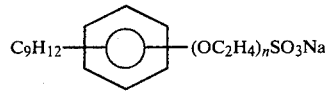

| Name | n | Conversion of Sulfite | Conversion of Sulfonate |
|---|---|---|---|
| Igepal CO-630 | 9 | 92 | 71 |
| Igepal CO-730 | 15 | 48 | 37 |
| Igepal CO-850 | 20 | 76 | 34 |

Although a comparison of sulfonate conversion by methylene blue activity may not be accurate through the Igepal CO series, the presence of unreacted sulfite indicates a reduced reactivity of the chlorine terminated nonionic with increasing chain length whatever the product distribution from the chloride might be. Inclusion of a more reactive halogen (NaBr, NaI) can be employed to improve the nonionic reactivity by in situ halogen exchange.

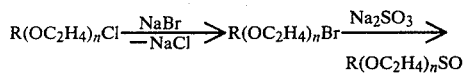

$$R(OC_2H_4)_nSO_3Na + NaBr$$

Alternatively, the charge of $Na_2SO_3$ can be increased to increase the reactive collision frequency. In the case of Igepal CO-850 a 50% excess of sulfite would result in an increase in salt content in the product of only 2.0%, thus increasing the salt content in the final product but to a tolerable level.

1. Preparation of Alfol 1012+3 EO Ether Sulfonate (a) Chlorination

A 1 l. r.b. flask equipped with mechanical stirrer, thermometer, dropping funnel and condenser adapted to a caustic scrubber was charged with 600 gms of thionyl chloride (2.0 moles). To it were added 286 gms of thionyl chloride (2.4 moles) maintaining the reaction mixture 55° C. during addition. The mixture was then heated to 100° C. for 1 hour, the condenser removed and heated to 100°–110° C. with an air purge for 2½ hours. The appearance of the chloride was improved by the addition of 3 gms of 30% $H_2O_2$ at 80° C. and heating to 100°–110° C. for 15 minutes (VCS 15 initial; VCS 9.5 final). Analysis: Cl 11.67/11.2 (actual/theory).

(b) Sulfonation

A charge of 420 gms of the Alfol 1012+3 EO chloride (1.32 moles) was combined with 175 gms of $Na_2SO_3$ (1.39 moles), 100 ml of distilled water and 4.5 gms of 50% NaOH in a 1 gallon autoclave and reacted at 160°±5° C. for 20 hours. Stirring speed was 1750 rpm. The product was cooled to 40° C. and discharged. It was a viscous, light yellow liquid (VCS 4+) having a methylene blue (M.B.) activity of 25.7% (80.8%) based on a molecular weight of 386, a chloride content of 5.27% and a pH of 5.3 (20% solution). The excess sulfite was removed by adding 16.5 gms of 30% $H_2O_2$ at 30°–40° C. and the pH adjusted to 7.2 with 9.5 gms of 50% NaOH. The final product properties include 1.83% $Na_2SO_4$, 4.64% NaCl and 36.2% total solids.

2. Preparation of Alfol 12+4 EO Ether Sulfonate (a) Chlorination

A 1 l. round bottom flask equipped with mechanical stirrer, thermometer, dropping funnel and condenser adapted to a caustic scrubber was charged with 500 gms (1.38 moles) of Alfol 12+4 EO. To it were added 205 gms (1.73 moles) of thionyl chloride at a rate which conveniently maintained the temperature below 55° C. The mixture was then heated to 100°–105° C. for 4 hrs. When the OH band had been removed, the condenser was removed and the chlorosulfite heated to 100°–110° C. with an air purge to remove the $SO_2$ formed. The air purging and heating were continued for 4 hours. The appearance of the resultant organic chloride (VCS 12) was improved by the addition of 5 gms of 30% $H_2O_2$ at 70° C. and heating to 100°–105° C. for 10 minutes (final VCS of 8). Analysis: Cl, 9.34/9.33 (actual/theory).

(b) Sulfonation

A charge of 440 gms of the Alfol 12+4 EO chloride (1.16 moles) was combined with 158 gms of $Na_2SO_3$ (1.25 moles), 880 gms of distilled water and 8 gms of 50% NaOH in a 1 gallon autoclave and reacted at 165°±5° C. for 20 hours. Stirring speed was 1750 rpm. The product was cooled to 60° C. and discharged. It was a pale yellow viscous, clear liquid which solidified on standing overnight (it has a m.pt. of 28° C. and if diluted to a M.B. activity of 19% remains a liquid at room temperature). Preliminary data indicated a methylene blue activity of 28.8% (72.7%) based on a molecular weight of 448, and an inorganic chloride content of 4.32%. The excess sulfite was removed by adding 22 gms of 30% $H_2O_2$ and stirring at room temperature and the pH was adjusted to 7.3 to 4.5 gms of 50% NaOH. Final product properties include 1.87% $Na_2SO_4$, 2.95% NaCl, 40.2% total solids, 4.76% nonionics.

3. Preparation of Alfol 1214+6 EO Ether Sulfonate (a) Chlorination

A 2 l. flask equipped with mechanical stirrer, thermometer, dropping funnel and condenser adapted to a caustic scrubber was charged with 752 gms of Alfol 1214+6 EO (2.0 moles). To it were added 286 gms of thionyl chloride (2.4 moles) maintaining the reaction temperature below 55° C. When the addition was completed, the reaction mixture was heated to 100° C. for ½ hour, the condenser removed and heating at 100°–110° C. continued for three hours under an air purge (subsurface) to remove $SO_2$. The appearance of the chloride was improved by the addition of 40 gms of 30% $H_2O_2$ added at 65° C. followed by heating to 90° C. for 15 min (VCS 13.5 initial; VCS 7 final). Analysis: Cl 8.61/9.00 (actual/theory).

(b) Sulfonation

A 10 gm portion of the above chloride was dissolved in ethanol and titrated to a pH of 10., with 0.1 N NaOH (12.6 ml). A charge of 711 gms of the Alfol 1214+4 EO chloride (1.80 moles) was combined with 238 gms of $Na_2SO_3$ (1.89 moles), 1500 ml distilled water and 12 gms of 50% NaOH in a 1 gallon autoclave and reacted at 160°±5° C. for 20 hours at 1750 rpm. The product was cooled to 40° C. and discharged. It was a 2 layer system initially (viscous yellow liquid—top layer hazy, bottom layer clear) which solidified on standing. As such it had a M.B. activity of 24.4% (72.2%) based on a molecular weight of 462, a chloride content of 4.68% (101%) and a pH of 6.6 (20% solution). The excess sulfite was removed by the addition of 54 gms of 30% $H_2O_2$ and the pH was adjusted to 7.2 (20% sol'n) by addition of 10 gms 50% caustic. The final product properties include 2.68% $Na_2SO_4$, 4.50% NaCl and 39.5% total solids. The sample is a white solid at room temperature at this concentration. Dilution with distilled water to a M.B. activity of 13.3% affords a clear, yellow, liquid product.

4. Preparation or oxo-Tridecyl+4.2 EO Ether Sulfonate (a) Chlorination

A 2 l. flask equipped with mechanical stirrer, thermometer, dropping funnel and condenser adapted to a caustic scrubber was charged with 800 gms of emulphogene BC-420 (2.4 moles. To it were added 343 gms of thionyl chloride (2.88 moles) maintaining the temperature below 55° C. during addition. The reaction mixture was then heated to 100°–105° C. for ½ hour, the condenser removed and heating to 100°–105° C. continued for 1½ hours with an air purge (subsurface) to remove $SO_2$. The appearance of the chloride was improved by the addition of 30 gms of 30% $H_2O_2$ at 70° C. and heating to 100° C. for ½ hour (VCS 18 initial; VCS 12 final). The final inorganic chloride was 0.1%. Analysis Cl 9.91/10.1 (actual/theory).

(b) Sulfonation

A charge of 445 gms of the Emulphogene BC-420 chloride (1.27 moles) was combined with 168 gms of $Na_2SO_3$ (1.33 moles), 1000 ml of distilled water and 10 gms of 50% NaOH in a 1 gallon autoclave and reacted at 165°±50° C. for 20 hours at 1750 rpm. The product was cooled to 40° C. and discharged. It was a viscous gelatenous material having a M. B. activity of 22.9% (70.1%) based on a molecular weight of 418, an inorganic chloride content of 4.68% and a pH of 6.7 (20% solution). The excess sulfite was removed by the addition of 72 gms of 30% $H_2O_2$ and the pH adjusted to 7.5 with 9 gms of 50% NaOH. The final product properties include 2.36% $Na_2SO_4$, 4.41% NaCl and 34.6% total solids. It offers a clear yellow solution with 25% ethanol. Dilutions to 13% M.B. activity with water, also provide a clear liquid above 70° C. which, however, clouds on slight cooling.

5. Preparation of Nonylphenol+9 EO Ether Sulfonate (a) Chlorination

A 3 l. flask equipped with mechanical stirrer, thermometer, dropping funnel and condenser adapted to a caustic scrubber was charged with 2000 gms of Igepal CO-630 (3.28 moles). To it were added 540 gms of thionyl chloride (4.54 moles) maintaining the reaction temperature below 60° C. When the addition was completed the reaction mixture was heated to 120° C. for ½ hour at which time an IR revealed no OH band at 3500 $cm^{-1}$. The condenser was removed and heating at 100°–110° C. continued with removal of $SO_2$ by a subsurface nitrogen purge. The heating was continued for a total of 7 hours, whereupon conversion to the chloride was essentially complete. The appearance of the chloride was improved by bleaching with 50 gms of 30% $H_2O_2$ at 70°–90° C. for 15 minutes (VCS 18 initial, VCS 13 final). Analysis: Cl 5.51/5.63 (actual/theory).

(b) Sulfonation

A charge of 638 gms of the Igepal CO-630 chloride (1.0 mole) was combined with 131 gms of $Na_2SO_3$ (1.0 mole), 1200 ml of distilled water and 6.0 gms of 50% NaOH in a 1 gallon autoclave and reacted at 160°±5° C. for 20 hours at 1750 rpm. The product was cooled to 40° C. and discharged. It was a very viscous clear yellow liquid having a M.B. activity of 25.5% (71.4%) based on a molecular weight of 698, a chloride content of 2.98% (101%) and a VCS of 2. The excess sulfite was removed by the addition of 16 gms of 30% $H_2O_2$ and the pH adjusted to 7.4 with 9 gms of 50% NaOH. The final product properties include 1.48% $Na_2SO_4$, and 40.3% total solids.

PREPARATION OF NONYLPHENOL AND 20 E.O. ETHER SULFONATE

The procedure employed for producing the nonylphenol 9 E.O. ether sulfonate can be followed using Igepal CO-850 and thionyl chloride in a 1 to 1.5 mole ration in the chlorination procedure and a 1 to 1 Igepal CO-850 chloride to sodium sulfite mole ratio in the sulfonation procedure.

PREPARATION OF NONYLPHENOL AND 40 E.O. ETHER SULFONATE

The procedure for producing the nonylphenol 9 E.O. ether sulfonate can be followed, using Igepal CO-890 in approximately a 1 to 1.5 mole ratio with thionyl chloride. The sulfonation step can employ the resultant chloride of Igepal CO-890 in a 1 to 4 mole ratio with sodium sulfite.

The theory of the invention is not fully understood and discussions of the theory of operation are for the purposes of contributing clarity and understanding and are not intended by way of limitation.

Table I sets forth experimental results of the production of high solids content vinyl acetate emulsions using various surfactants. The term "high solids content" as employed herein means emulsions in which the solids constitutes at least 40% by weight of the composition.

The sodium sulfonate of the surfactants sold under the trademark IGEPAL CO-630 by GAF Corporation was found to coagulate during its formulation into a vinyl acetate latex but only during the last stages of addition thus showing a higher level of compatibility with vinyl acetate than many other surfactants, but, nevertheless, failing to produce the required results.

PROCEDURE I

The latex was produced by blending in a two liter resin kettle, 28 grams of the surfactant (based on 100% methylene blue activity) and 536 grams of total water (including water present in a surfactant). The solution was stirred and the pH was adjusted to 7.0 with KOH. Nitrogen purging was initiated and the solution was heated to 80° C. When 80° C. was achieved, 3.3 grams of ammonium persulfate was added to the kettle and the drop-wise addition of 726 grams of vinyl acetate was begun. Addition of the vinyl acetate proceeded over a 3.5 hour period, during which time the 80° C. temperature was maintained and a stirring rate of the latex was kept at the range of 350–400 RPM. After addition of vinyl acetate was complete, two 0.3 gram samples of ammonium persulfate were added 15 minutes apart. The latex was then cooled to room temperature and filtered to a 60 mesh screen.

PROCEDURE II

To produce a 62% solids poly(vinyl acetate) latex, the foregoing procedure was followed, except that the quantity of vinyl acetate was increased by 17%, from 726 to 850 grams.

Analytical Techniques (a) Coagulum—Solids which were held in the 60 mesh screen are thoroughly washed, dried in a 110° oven for two hours and weighed. When the amount of solid present is too small to collect, or if the coagulum is water soluble, a qualitative description is recorded.

(b) Mechanical Stability—The filtered latex is placed in an Osterizer blender, and blended for 10 minutes at maximum speed. If the latex coagulates during this time, mechanical stability is no good.

(c) Brookfield Viscosity—The filtered latex sample is poured into a 8 oz. sample bottle. The viscometer is fitted with the proper spindle, set for the proper rpm, and lowered into the latex. The viscosity is read directly from a dial.

(d) Solids—Three weighing pans are tared, about 5 g. of the latex is placed in each, and the samples are placed in a 110°–120° C. oven for 2 hours. The dried sample is then weighed, and % solids is calculated from (dry weight/wet weight)×100.

(e) Surface tension is measured with a Fisher Tensiomat.

(f) pH is measured with any available pH meter.

(g) Turbidity—A sample of the latex is placed in a test tube and diluted with a 1% solution of sodium lauryl sulfate to give an absorbance reading of between 0.5 and 0.8 at 450 mm in a Spectronic 20 visible spectrometer. Absorbance readings are made at 450, 500, 550 and 600 mm. The slope of a best fit straight line for the relationship of log (absorbance) versus log (wavelength) is determined with a least squares computer program. This slope is recorded as turbidity.

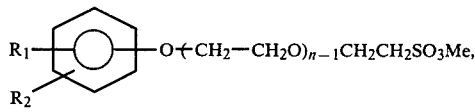

wherein:
$R_1$ is an alkyl group having from 6 to 18 carbons;
$R_2$ is H or an alkyl group having from 6 to 12 carbons;
$n$ is greater than 9; and
Me is a monovalent cation selected from the group consisting of $NH_4$, Na, Li and K,
the weight ratio of water to vinyl acetate being predetermined such that the resultant emulsion contains at least 40% by weight of solids.

2. The method of claim 1, wherein $R_1$ and $R_2$ do not have a combined total of greater than 24 carbons.

3. The method of claim 1, wherein $n$ is between about 15 and 30.

4. The method of claim 1, wherein the surfactant is the sodium salt of nonyl phenoxy poly(ethyleneoxy) sulfonate and contains on the order of 20 ethylene oxide units.

5. A stable aqueous emulsion of a vinyl acetate polymer produced by polymerizing a monomer charge comprising:
(a) water;
(b) vinyl acetate monomer; and
(c) at least about 0.1 percent by weight based on the weight of the vinyl acetate monomer, of a surfactant having the formula:

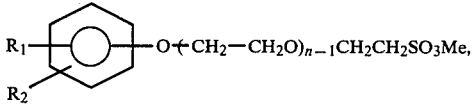

wherein:
$R_1$ is an alkyl group having from 6 to 18 carbons;
$R_2$ is H or an alkyl group having from 6 to 12 carbons;
$n$ is greater than 9; and

TABLE I

| SURFACTANT | VINYL ACETATE LATEX-% SOLIDS | COAGULUM | MECHANICAL STABILITY | BROOKFIELD VISCOSITY | POLYVINYL ACETATE LATEX % SOLIDS | pH | SURFACE TENSION |
|---|---|---|---|---|---|---|---|
| Igepal CO-630 - Sulfonate | 55 | 100%* | — | — | — | — | — |
| Igepal CO-850 - Sulfonate | 55 | None | OK | 70(1-60) | 56.8 | 3.0 | 43.4 |
| Igepal CO-850 - Sulfonate | 55 | 5.0 gms | OK | 95(1-60) | 56.6 | 6.9 | 38.5 |
| Igepal CO-850 - Sulfonate | 55 | None | N.G. | 850(3-60) | — | — | 50.0 |
| Igepal CO-850 - Sulfonate | 55 | None | OK | 85(1-60) | 55.6 | 3.0 | 42.0 |
| Igepal CO-850 - Sulfonate | 62 | None | OK | 385(1-12) | 62.8 | 2.9 | 44.0 |
| Igepal CO-890 - Sulfonate | 55 | Very Slight** | OK | 120(1-30) | 56.2 | 3.1 | 47.0 |
| (Alfol 1012 + 3 E.O.) Sulfonate | 55 | 100% | — | — | — | — | — |
| (Alfol 12 + 4 E.O.) Sulfonate | 55 | 100% | — | — | — | — | — |
| (Alfol 1214 + 6 E.O.) Sulfonate | 55 | 100% | — | — | — | — | — |
| Emulphogene BC-720 Sulfonate | 55 | 100% | — | — | — | — | — |
| (Oxotridecyl + 4.2 E.O.) Sulfonate) | 55 | 100% | — | — | — | — | — |

*In final stages of addition
**Coagulated after 24 hours storage

What is claimed is:

1. The method of producing aqueous polymer emulsions comprising: contacting a mixture of water, vinyl acetate monomer and at least about 0.1 percent by weight of the vinyl acetate monomer of a surfactant having the formula:

Me is a monovalent cation selected from the group consisting of $NH_4$, Na, Li and K,
said water comprising less than about 60% by weight of the emulsion.

6. The emulsion of claim 5, wherein $R_1$ and $R_2$ have a combined total of no greater than 24 carbons.

7. The emulsion of claim 6, wherein $n$ is between about 15 and 30.

8. The emulsion of claim 5, wherein Me is sodium.

* * * * *